(12) United States Patent
Pimonov et al.

(10) Patent No.: US 9,638,649 B2
(45) Date of Patent: May 2, 2017

(54) DETERMINATION OF LOCAL CHANGES OF CONCENTRATION OF ADMIXTURES IN FLUID FLOW

(71) Applicant: SCHLUMBERGER TECHNOLOGY CORPORATION, Sugar Land, TX (US)

(72) Inventors: Evgeny Pimonov, Moscow (RU); Alexander Starostin, Moscow (RU); Oleg Yurievich Dinariev, Moscow (RU); Dmitry Alexandrovich Korobkov, Moscow (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 711 days.

(21) Appl. No.: 14/015,923

(22) Filed: Aug. 30, 2013

(65) Prior Publication Data
US 2014/0067281 A1    Mar. 6, 2014

(30) Foreign Application Priority Data

Sep. 3, 2012 (RU) .................................. 2012137227

(51) Int. Cl.
*G01N 27/00*  (2006.01)
*G01N 27/08*  (2006.01)

(52) U.S. Cl.
CPC .............. *G01N 27/00* (2013.01); *G01N 27/08* (2013.01)

(58) Field of Classification Search
CPC .................................. G01N 27/08; G01N 27/00
See application file for complete search history.

(56) References Cited

U.S. PATENT DOCUMENTS 8,440,093 B1 *  5/2013  Nassef ............. B01L 3/502707
                                                   216/84
9,132,392 B2 *  9/2015  Narushima ............. B01J 10/00

FOREIGN PATENT DOCUMENTS

RU      2281484 C1     8/2006

OTHER PUBLICATIONS

Hutchins et al., "A Continuous Flow Input Function Detector for H215O Blood Flow Studies in Positron Emission Tomography" IEEE Transactions on Nuclear Science, vol. 33, No. 1, Feb. 1986.*
Gas, et al., "Optimization of the High-Frequency Contactless Conductivity Detector for Capillary Electrophoresis", Electrophoresis, vol. 23, 2002, pp. 3520-3527.

(Continued)

Primary Examiner — Alexander Satanovsky
Assistant Examiner — John Kuan

(57) ABSTRACT

The invention allows determining a local change of an admixture concentration in a fluid flow at an entrance to a measurement cell. The change of the admixture concentration in time inside the measurement cell is first determined for a fluid containing the admixture, the change of concentration of which in time at the entrance to the measurement cell is known. Then, an impulse response of the cell is found applying the deconvolution method. The change of the admixture concentration inside the measurement cell is then determined for a fluid being studied with an unknown concentration of the admixture at the entrance. The unknown concentration is determined using the impulse response of the measurement cell and the change of the admixture concentration inside the cell.

2 Claims, 5 Drawing Sheets

(56) References Cited

OTHER PUBLICATIONS

Gopakumaran, et al., "A New Technique to Measure and Track Blood Resistivity in Intracardiac Impedance Volumetry", Journal of Clinical Monitoring, vol. 13, 1997, pp. 363-371.
Gringarten, "From Straight Lines to Deconvolution: The Evolution of the State of the Art in Well Test Analysis", SPE 102079—SPE Annual Technical Conference and Exhibition, San Antonio, Texas, Sep. 24-27, 2006, pp. 41-62.
Huang, et al., "Design of capacitively coupled contactless conductivity detection sensor", Flow Measurement and Instrumentation, vol. 27, 2012, pp. 67-70.
Levy, et al., "Measurement and Analysis of Non-Fickian Dispersion in Heterogeneous Porous Media", Journal of Contaminant Hydrology, vol. 64, 2003, pp. 203-226.
Lichtenberger, "Field Applications of Interwell Tracers for Reservoir Characterization of Enhanced Oil Recovery Pilot Areas", SPE 21652—Production Operations Symposium, Oklahoma City, Oklahoma, Apr. 7-9, 1991, pp. 209-225.
Pop, et al., "On-Line Electrical Impedance Measurement for Monitoring Blood Viscosity during On-Pump Heart Surgery", European Surgical Research, vol. 36, 2004, pp. 259-265.

\* cited by examiner

DETERMINATION OF LOCAL CHANGES OF CONCENTRATION OF ADMIXTURES IN FLUID FLOW

CROSS-REFERENCE TO RELATED APPLICATION

This application claims priority to Russian Application No. 2012137227 filed Sep. 3, 2012, which is incorporated herein by reference in its entirety.

FIELD

The invention is related to measurement methods and might be used in estimation of nonstationary concentration of admixtures in a particular fluid flow point.

BACKGROUND

It is known that the presence of an admixture changes various properties of a carrying fluid, such as density, color, radioactivity, magnetic and thermal properties and electrical resistivity. So, measurement of physical properties allows estimating a concentration of an admixture; in particular, compositions of a saline solution, a water-oil emulsion and other mixtures may be determined by measuring the electrical resistivity. The following concentration determining methods are known: visual (by admixture color), indirect (by flow conductivity), etc., (see, for example, M. Levy, B. Berkowitz, Measurement and Analysis of Non-Fickian Dispersion in Heterogeneous Porous Media, Journal of Contaminant Hydrology//2003, 64, pp. 203-226; Gas B, Zuska J, Coufal P, van de Goor T. Optimization of the High-Frequency Contactless Conductivity Detector for Capillary Electrophoresis, Electrophoresis//2002, v. 23, pp. 3520-3527).

The main problem of the known method is the averaged nature of measurements, i.e., a significant time interval determined by dimensions of a measurement cell within which an admixture concentration may change significantly. The disclosed method provides improved accuracy of determining the concentration of an admixture without changing configuration of a measurement cell.

The disclosed method for determining local changes of concentration of an admixture in a fluid flow comprises injecting the fluid through a measurement cell; the fluid contains an admixture a change of concentration of which in time at an inlet to the measurement cell is known. The admixture concentration change in time is determined in the measurement cell, then, an impulse response of the measurement cell is recovered applying a method of deconvolution. A fluid being studied is injected through the measurement cell and a change of the admixture concentration in time in the fluid flow is determined in the measurement cell. The change of the admixture concentration in time in the flow of the fluid being studied at the inlet to the cell is found with the following equation:

$$\int_0^t K(t-\tau)I(\tau)d\tau = R_\sigma(t)$$

where $\tau$—an integration variable, t—time, I(t)—change of the admixture concentration in the flow of the fluid being studied at the inlet to the cell, $R_\sigma(t)$—change of the admixture concentration in the flow of the fluid being studied in the measurement cell, K(t)—the impulse response of the measurement cell.

A dependence of a physical property of the fluid on a concentration of the admixture may be determined preliminarily; in this case, the change of the admixture concentration in the fluid flow in the measurement cell is determined by measuring the physical property of the fluid.

The fluid property being measured is an electrical resistivity, a density, a radioactivity, etc.

A quality of the measurement cell may also be estimated; for this purpose, a difference between the concentration measured in the measurement cell and the concentration at the inlet to the measurement cell is determined and the quality of the measurement cell is estimated based on the determined difference.

The quality of the measurement cell may also be estimated by determining the impulse response of the measurement cell by the Fourier transformation and comparing the Fourier transformation from the function K(t) with the constant $1/\sqrt{2\pi}$.

DETAILED DESCRIPTION

Figure 1:
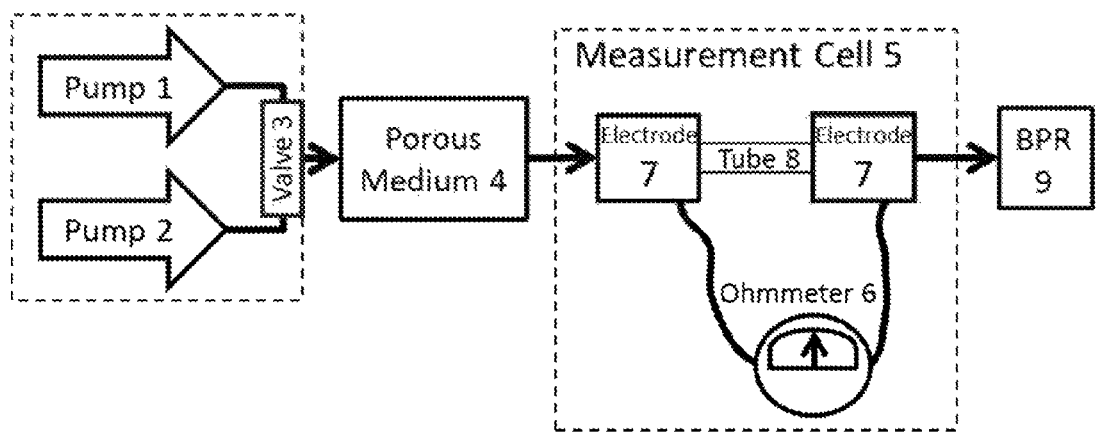
FIG. 1 shows an example of an experimental system with a measurement cell.

An embodiment of the disclosure by measuring a fluid electrical resistivity is provided. In this embodiment a measurement cell comprising a tube made from a dielectric material and two electrodes being in contact with the fluid is used (FIG. 1). Such a cell design is used in a number of measurements (see, for example, Zhiyao Huang, Jun Long, Wenbo Xu, Haifeng Ji, Baoliang Wang, Haiqing Li, Design of Capacitively Coupled Contactless Conductivity Detection Sensor//2012, Flow Measurement and Instrumentation, in press). The fluid electrical resistivity inside the tube depends on the concentration of the admixture in the flow. So, the resistivity measurements allow determining the admixture concentration within the volume limited by the tube and the electrodes. The admixture concentration at the inlet to the cell (a true concentration) may differ considerably from the readings for the cell measuring the concentration within the volume due to the heterogeneity of the concentration field. When using such a cell, a difference between the cell readings and the true admixture concentration at the inlet to the cell should be reduced.

The measurement cell is a signal processing system. Presumably, the processing system possesses a linearity property and does not depend on time (a Linear Time Independent System, hereinafter LTIS; for examples of such systems see J. P. Hespanha, Linear Systems Theory//2009, Princeton University Press, 263 p., ISBN 978-0-691-14021-6). If a LTIS impulse transient function is known, then for any measured output signal of LTIS (a response to an input signal) the corresponding input signal might be restored with a deconvolution method. In its turn, the impulse transient function of LTIS may also be calculated with the deconvolution method measuring the LTIS response to an input signal known in advance.

The input signal of this LTIS is the admixture concentration in the carrying fluid at the inlet to the cell; the output signal is the admixture concentration calculated based on the measured resistivity of the carrying fluid. The LTIS is peculiar of an impulse transient function often called an impulse response of the system.

The invention allows determining a change of the admixture concentration in a carrying fluid at an inlet to a measurement cell. The measurement procedure involves a number of stages. A dependence of an electrical resistivity of the fluid being studied on concentration of the admixture is determined preliminarily. A fluid, for which a change of the admixture concentration in time at the inlet to the cell is known, is injected through the cell, and a system output signal is registered (i.e., of the measurement cell). Then, a system impulse transient function is determined applying a deconvolution method. A system output signal is then registered (i.e., a resistivity) for the fluid being studied with an unknown change of the admixture concentration at the inlet. Finally, an unknown change of the admixture concentration at the inlet to the cell is found applying the deconvolution method and using the impulse transient function found before, and the concentration in the cell found during the resistivity measurements.

In an embodiment of the invention, an experimental system for reproduction of a flow with an admixture shown in FIG. 1 was used. The experimental system comprises a pump 1 for a fluid with a known change of an admixture concentration at an inlet to a measurement cell; a pump 2 for the fluid being studied, a concentration in which needs to be determined; a three-way valve 3; a porous medium 4; the measurement cell 5; an ohmmeter 6; electrodes 7; a dielectric material tube 8 and a backpressure system 9.

The admixture concentration field is time-dependent. Determination of a change of concentration in a particular flow point allows estimating the admixture dispersion inside a porous sample. The admixture concentration may be determined by the change of the fluid electrical resistivity inside the measurement cell. The concentration determination error is expressed in $\sigma$.

An empirical dependence of resistivity on concentration of the admixture is found in advance (for example, on a fluid salinity). The dependence is used for estimating the admixture concentration by, for example, the ohmmeter readings in determining the concentration of an electrically conductive admixture (FIG. 1).

A flow is used for which a dynamics of the admixture propagation is known and a change of the admixture concentration at the inlet to the measurement cell equal to i(t), where t is time, is known. The cell registers a resistivity change $r_o(t)$. So, both functions i(t) and $r_o(t)$ are known.

The performed experiment data are used for recovering an impulse response of the system K(t) (the impulse transient function of LTIS):

$$\int_0^t K(t-\tau)i(\tau)d\tau = r_o(t) \qquad (1)$$

$$\|r - r_o\| < \sigma$$

If i(t)≈1 in a known flow regime, a kernel is easily found based on the result of measurements as $$K(t) \approx \frac{dr}{dt}(t).$$

Otherwise, a deconvolution method should be used to recover the kernel K(t), i.e., solving the integral equation assuming smoothness of the required function.

An experiment is then performed, in which a propagation of the admixture in the flow should be investigated. A change of the admixture concentration at the inlet to the measurement cell is I(t); a change of the concentration registered during the measurements is R(t). The function I(t) is unknown.

The input signal I(t) is to be found with the known transient impulse function K(t) and the output signal R(t) in the form of the measured concentration (see equation (2) below). The problem solution is the function I(t), which estimates the local change of the admixture concentration in the flow.

$$\int_0^t K(t-\tau)I(\tau)d\tau = R_\tau(t) \qquad (2)$$

A difference between the input and the output signals may serve as an estimate of the quality of the measurement cell. If the set of measurements $\{I''(t), R''(t)\}$ is available, the difference $R''(t) - I''(t)$ for the flows under study may be calculated (n is the experiment number). This allows estimating the measurement cell quality. The lower is the difference, the higher—the measurement cell quality.

The measurement cell quality may also be estimated after recovering the impulse response. The highest measurements quality corresponds to the case when $R_o(t)=I(t)$. Using the equation (2), we get $K(t)=\delta(t)$, where $\delta(t)$ is the Dirac function. It is known that the Fourier transformation for the Dirac function is $F[\delta(t)]=1/\sqrt{2\pi}$. Thus, the closer the Fourier transformation from the function K(t) to the constant $1/\sqrt{2\pi}$, the higher the measurements quality. The distance between the functions may be estimated, for instance, by the $L^2$-norm:

$$\|f_1 - f_2\| = \left(\int_0^t (f_1(\tau) - f_2(\tau))^2 d\tau\right)^{\frac{1}{2}}$$

The disclosed procedure was applied in a study of flooding of a core with a brine of various concentrations. The 40 g/l NaCl solution was used as a basic fluid; the admixture was modeled with 60 g/l NaCl solution. A core sample (a porous rock sample) was put in a sealed core holder. The measurement cell was placed successively behind the core holder in the flow pattern and registered the admixture concentration in the flow behind the core holder.

Figure 2:
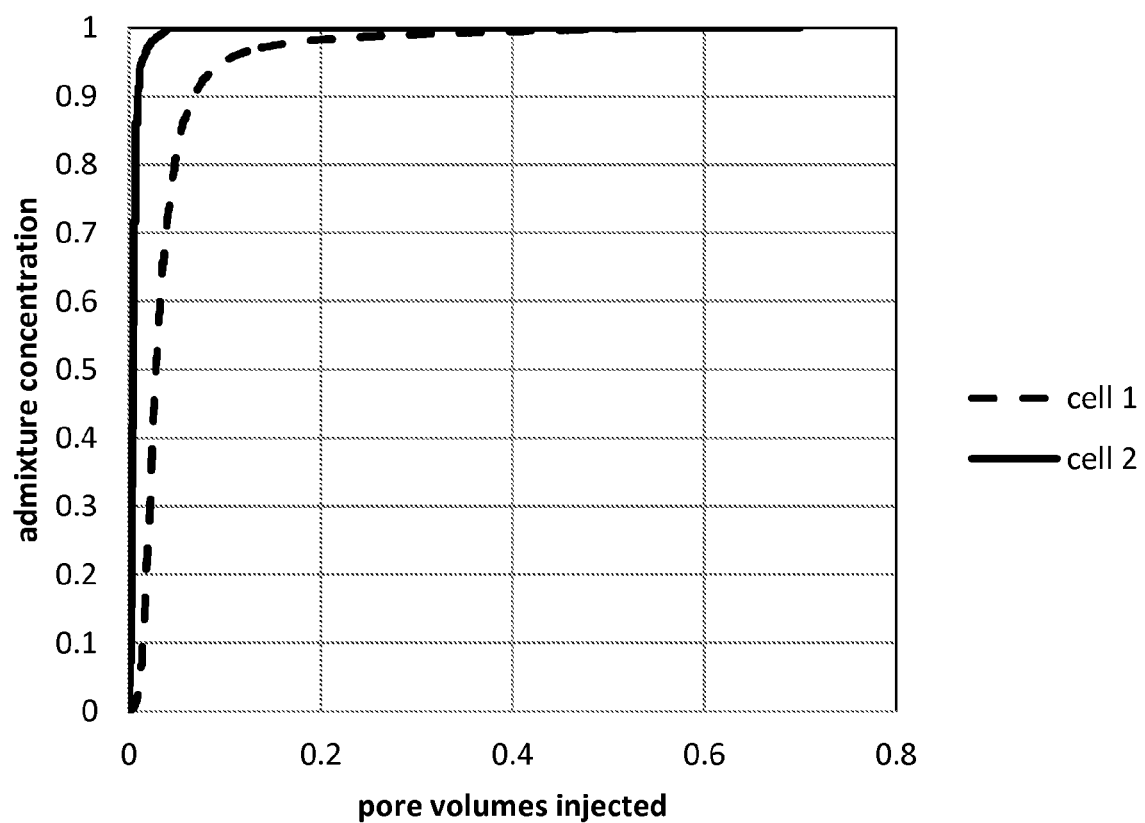
FIG. 2 shows results of measuring the admixture concentration in the fluid for two measurement cells.

The first measurement cell (cell 1) consisted of a plastic tube with steel electrodes on the ends (FIG. 1). A known flow regime was a propagation of the admixture in the measurement cell with no core provided in the flow pattern. The concentration at the inlet to the measurement cell changed abruptly from 0 to 1, so the input signal is the Heaviside function. The signal registered in the measurement cell is the result of smoothing the input signal. The first cell has the relaxation time, within which the readings changed from 0 to 1 at an abrupt change of the concentration at the inlet. The time scale was the time to inject a pore volume of the core sample; and it is equal to 5 s for 2 cm³/min pumping rate (FIG. 2, the cell 1).

Figure 3:
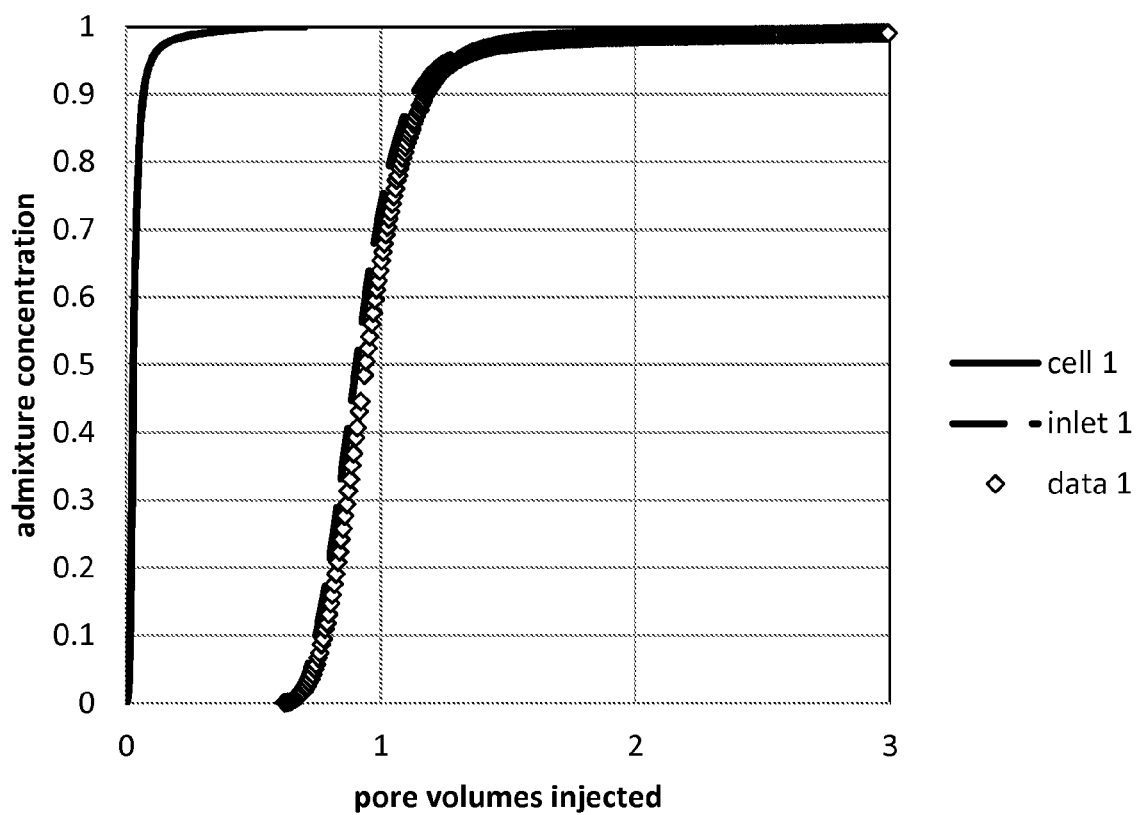
FIG. 3 shows results of measuring the admixture concentration in the fluid in a first cell and results of determining the concentration at the inlet to the measurement cell applying the disclosed method.

The use of the porous material (core) in the experiment results in washing the front out with smooth increase of the concentration at the outlet from the core holder. The concentration at the inlet to the cell was estimated applying the disclosed method (FIG. 3, the cell 1). It differed from the measured concentration considerably (the absolute error between the actual concentration at the inlet to the cell and the measured concentration was 10%).

Figure 4:
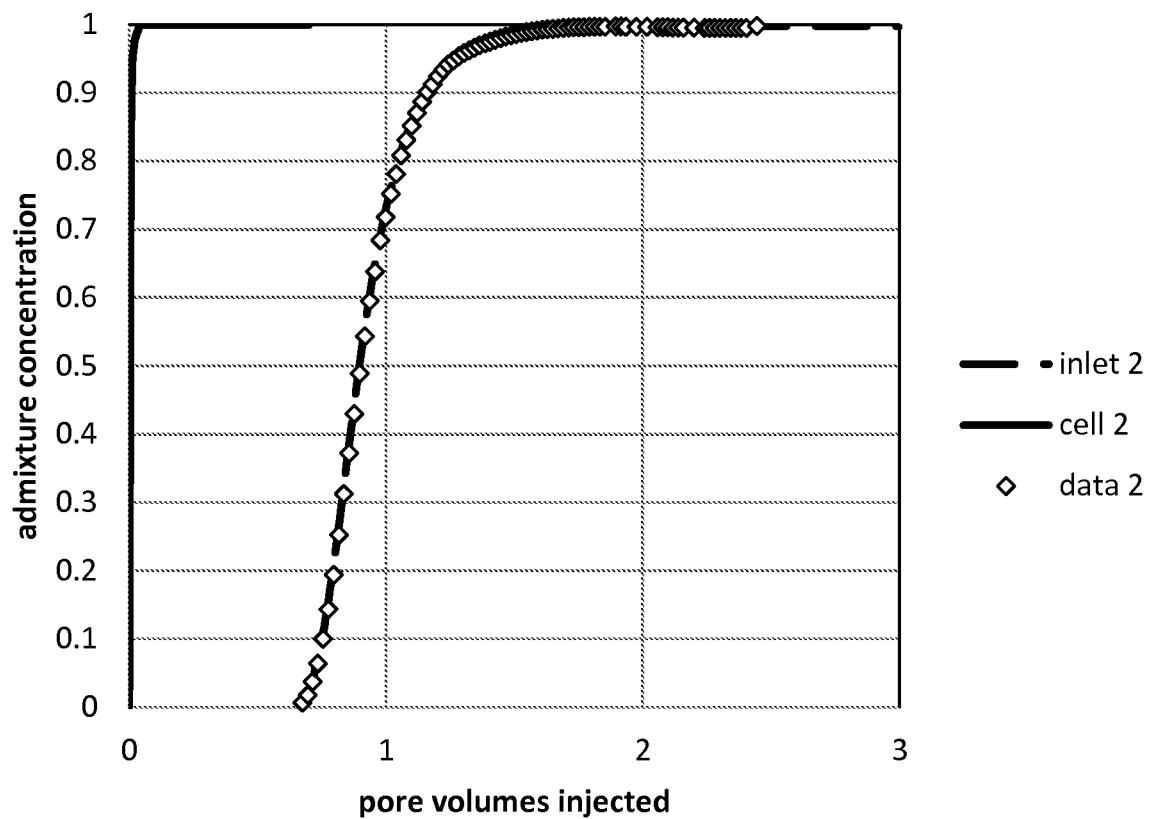
FIG. 4 shows results of measuring the admixture concentration in the fluid in a second measurement cell and results of determining a true concentration applying the disclosed method.
Figure 5:
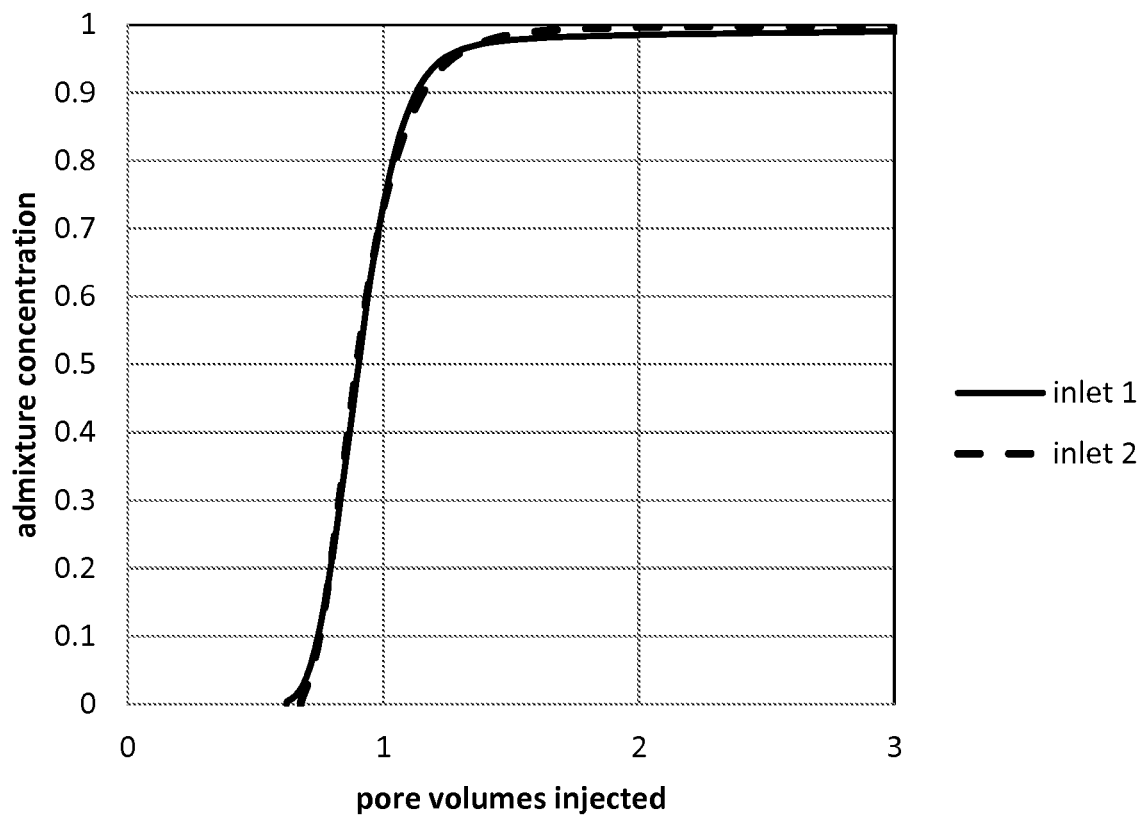
FIG. 5 shows results of determining a true concentration in the two cells applying the disclosed method.

The disclosed method was checked by comparing the results for two different measurement cells. The core flooding experiment was repeated using an improved measurement cell, in which the plastic tube was replaced with a glass tube of a smaller volume (FIG. 4, FIG. 5, the cell 2). The improved cell had a lower relaxation time compared to the first cell (FIG. 2, the cell 2). The method was applied to the concentrations registered with two different cells for the purpose of estimating the admixture concentration at the inlet to the measurement cell. In the course of the experiment it was found that the recovered true admixture concentrations at the inlet were less than 3% different. The study performed with the application of the disclosure showed that the improved cell increased the quality of measurements and provided the precision required for the core flooding experiment.

The difference between the input and the output signals may serve as an estimate of the measurement cell quality. The input signal is recovered with the disclosed method applying the deconvolution method. The difference between the signals may be calculated with various functional norms, for example, the norm $L^2$ equal to the integral of the square of the differences of signals by a time interval. The minimum value of the difference corresponds to the most precise measurement. Thus, when processing a series of experiment data applying the deconvolution method we may estimate the quality of the measurement cell.

The invention claimed is:

1. A method for determining local changes of concentration of an admixture in a fluid flow, comprising:
   determining an empirical dependence of electrical resistivity of a fluid on concentration of the admixture,
   injecting the fluid containing the admixture through a measurement cell, wherein the measurement cell is made in the form of a tube of a dielectric material disposed between two electrodes in contact with the fluid and wherein a change of concentration of the admixture in time in the flow of the fluid at an inlet to the measurement cell is known,
   detecting electrical resistivity of the fluid in the measurement cell during the injection,
   determining a first change of concentration of the admixture in time in the measurement cell using the determined empirical dependence of electrical resistivity of the fluid on the admixture concentration,
   recovering an impulse response of the measurement cell by applying a deconvolution method, based on the determined first change of concentration of the admixture in time in the measurement cell,
   injecting through the measurement cell the fluid with an unknown change of concentration of the admixture in time in the flow of the fluid at the inlet to the measurement cell,
   detecting electrical resistivity of the fluid with the unknown change of concentration of the admixture in time in the measurement cell during the injection,
   determining a second change of concentration of the admixture in time in the measurement cell using the determined empirical dependence of electrical resistivity of the fluid on the admixture concentration, and
   determining the unknown change of concentration of the admixture in time in the flow of the fluid at the inlet to the measurement cell with the following equation:

$$\int_0^t K(t-\tau)I(\tau)d\tau = R_\sigma(t)$$

where $\tau$ is an integration variable, t is time, I(t) is the unknown change of concentration of the admixture in the fluid flow at the inlet to the measurement cell, $R_\sigma(t)$ is the determined second change of concentration of the admixture in the fluid flow in the measurement cell, and K(t) is the recovered impulse response of the measurement cell.

2. The method of claim 1, wherein additionally a quality of the measurement cell is estimated.

* * * * *